United States Patent
Nguyen et al.

(10) Patent No.: US 11,160,158 B1
(45) Date of Patent: *Oct. 26, 2021

(54) COMPACT, HIGH-EFFICIENCY ACCELERATORS DRIVEN BY LOW-VOLTAGE SOLID-STATE AMPLIFIERS

(71) Applicant: TRIAD NATIONAL SECURITY, LLC, Los Alamos, NM (US)

(72) Inventors: Dinh Nguyen, Los Alamos, NM (US); Cynthia Buechler, Los Alamos, NM (US); Gregory Dale, Los Alamos, NM (US); John Lewellen, Los Alamos, NM (US)

(73) Assignee: TRIAD NATIONAL SECURITY, LLC, Los Alamos, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/792,014

(22) Filed: Feb. 14, 2020

Related U.S. Application Data

(63) Continuation of application No. 15/819,504, filed on Nov. 21, 2017, now Pat. No. 10,568,196.

(60) Provisional application No. 62/425,025, filed on Nov. 21, 2016.

(51) Int. Cl.
*H05H 7/02* (2006.01)
*H05H 9/02* (2006.01)
*A61N 5/10* (2006.01)

(52) U.S. Cl.
CPC ............ *H05H 7/02* (2013.01); *H05H 9/02* (2013.01); *A61N 2005/1087* (2013.01); *H05H 2007/025* (2013.01); *H05H 2277/11* (2013.01)

(58) Field of Classification Search
None
See application file for complete search history.

(56) References Cited

U.S. PATENT DOCUMENTS

| | | | | |
|---|---|---|---|---|
| 3,147,396 A | * | 9/1964 | Goerz | H05H 9/02 315/5.42 |
| 4,107,617 A | * | 8/1978 | Tran | H05H 7/02 315/5.41 |
| 5,298,867 A | * | 3/1994 | Mestha | H03L 7/00 315/500 |
| 5,483,122 A | * | 1/1996 | Derbenev | H05H 7/06 315/5.41 |
| 5,497,050 A | * | 3/1996 | Cheo | H03F 3/60 315/5.41 |
| 5,637,966 A | * | 6/1997 | Umstadter | G21K 1/003 315/111.81 |

(Continued)

*Primary Examiner* — Amy Cohen Johnson
*Assistant Examiner* — Srinivas Sathiraju
(74) *Attorney, Agent, or Firm* — Lewis Roca Rothgerber Christie LLP

(57) ABSTRACT

A compact particle accelerator can include two or more cavities disposed along an axis of the particle accelerator, each of which is coupled to two or more drivers. The accelerator can also include a power supply coupled to the two or more drivers such that a particle beam traveling along the axis is accelerated. The power supply can be an interface with a commercial power outlet, battery power, or a combination thereof depending upon the use case. Example configurations of the accelerator include hand held or mobile devices that are capable of delivering up to and greater than a 1 MeV electron beam.

20 Claims, 6 Drawing Sheets

(56) References Cited

U.S. PATENT DOCUMENTS

| | | | | |
|---|---|---|---|---|
| 5,744,919 A | * | 4/1998 | Mishin | H05H 9/00 315/500 |
| 5,828,585 A | * | 10/1998 | Welk | G01C 21/28 702/96 |
| 6,922,019 B2 | * | 7/2005 | Leung | H01J 27/18 250/492.3 |
| 7,259,373 B2 | * | 8/2007 | Zani | B82Y 10/00 250/309 |
| 7,402,963 B2 | * | 7/2008 | Sliski | H05H 13/02 315/502 |
| 7,495,242 B2 | * | 2/2009 | Zani | B82Y 10/00 250/492.21 |
| 7,501,644 B2 | * | 3/2009 | Zani | B82Y 10/00 250/492.21 |
| 7,760,054 B2 | * | 7/2010 | Lewellen | H01P 7/06 333/227 |
| 7,898,193 B2 | * | 3/2011 | Miller | H05H 9/04 315/505 |
| 8,077,103 B1 | * | 12/2011 | Acosta | H01Q 15/04 343/756 |
| 8,111,025 B2 | * | 2/2012 | Whittum | H05G 1/04 315/505 |
| 8,311,187 B2 | * | 11/2012 | Treas | H05H 9/02 378/119 |
| 8,324,810 B2 | * | 12/2012 | Kazakov | H05H 7/06 315/39.51 |
| 8,666,015 B2 | * | 3/2014 | Gahl | H05H 3/06 376/159 |
| 8,878,432 B2 | * | 11/2014 | Chen | H05H 7/02 315/5.41 |
| 8,952,634 B2 | * | 2/2015 | Sliski | H05H 13/02 315/503 |
| 9,129,714 B2 | * | 9/2015 | Noonan | H05H 7/02 |
| 9,258,876 B2 | * | 2/2016 | Cheung | H05H 9/02 |
| 9,326,366 B2 | * | 4/2016 | Krasnykh | H05G 2/00 |
| 9,433,135 B2 | * | 8/2016 | Heid | H05K 9/00 |
| 9,474,144 B2 | * | 10/2016 | Harasimowicz | H05H 7/02 |
| 9,478,841 B2 | * | 10/2016 | Heid | H05H 9/00 |
| 9,622,333 B2 | * | 4/2017 | Nighan, Jr. | H05H 9/048 |
| 9,948,112 B2 | * | 4/2018 | Hao | H02J 50/12 |
| 10,015,874 B2 | * | 7/2018 | Mishin | H05H 9/047 |
| 10,135,236 B2 | * | 11/2018 | Schill, Jr. | H02H 5/005 |
| 10,211,505 B1 | * | 2/2019 | Lewellen, IV | H01P 5/18 |
| 10,568,196 B1 | * | 2/2020 | Nguyen | H05H 7/02 |
| 2008/0042784 A1 | * | 2/2008 | Lewellen | H01P 7/06 333/227 |
| 2008/0218102 A1 | * | 9/2008 | Sliski | H05H 13/02 315/502 |
| 2009/0302785 A1 | * | 12/2009 | Miller | H05H 9/04 315/505 |
| 2011/0188638 A1 | * | 8/2011 | Treas | H05H 7/02 378/137 |
| 2013/0127375 A1 | * | 5/2013 | Sliski | H05H 13/02 315/502 |
| 2013/0315379 A1 | * | 11/2013 | Treas | H05H 9/02 378/121 |
| 2014/0035588 A1 | * | 2/2014 | Botto | E21B 47/11 324/333 |
| 2014/0037065 A1 | * | 2/2014 | Botto | H05G 1/00 378/86 |
| 2015/0042244 A1 | * | 2/2015 | Back | H03B 1/02 315/500 |
| 2015/0359080 A1 | * | 12/2015 | Dolgashev | H05H 9/02 315/505 |
| 2016/0014877 A1 | * | 1/2016 | Sugahara | H05H 7/02 315/503 |
| 2016/0270203 A1 | * | 9/2016 | Ungaro | H05H 9/041 |
| 2017/0055338 A1 | * | 2/2017 | Saverskiy | H05H 7/08 |
| 2017/0071054 A1 | * | 3/2017 | Benson | H05H 7/08 |
| 2018/0124910 A1 | * | 5/2018 | Slubbers | H05H 7/18 |

* cited by examiner

COMPACT, HIGH-EFFICIENCY ACCELERATORS DRIVEN BY LOW-VOLTAGE SOLID-STATE AMPLIFIERS

CROSS-REFERENCE TO RELATED APPLICATION(S)

This is a continuation application of U.S. patent application Ser. No. 15/819,504, filed Nov. 21, 2017, now U.S. Pat. No. 10,568,196, which claims priority to and the benefit of U.S. Provisional Patent Application No. 62/425,025, filed on Nov. 21, 2016, the entire contents of which are hereby expressly incorporated herein by reference.

STATEMENT REGARDING FEDERALLY SPONSORED RESEARCH OR DEVELOPMENT

The United States government has rights in this invention pursuant to Contract No. 89233218CNA000001 between the United States Department of Energy/National Nuclear Security Administration and Triad National Security, LLC for the operation of Los Alamos National Laboratory.

FIELD

The present invention relates generally to the field of particle accelerator, and more particularly to the field of high performance, compact particle accelerators (e.g., in hand held or mobile devices).

BACKGROUND

There is an ever increasing need to reduce the size, weight, cost and complexity of particle accelerators in applications beyond the usual high-energy physics, nuclear physics and synchrotron light sources where the accelerator designs have been largely based on the traditional large, complex, high-voltage, high-gradient designs. As the use of particle beams becomes more diversified and commonplace, the limitations inherent within prior legacy designs are becoming more evident. In the medical field, for example, the availability of accelerators that can be used for imaging or therapeutic purposes is limited by their size and cost, and operational characteristics, such as whether the accelerator is a cyclotron or a linac, power consumption (typically in the MW level) and cooling requirements (water cooling towers or liquid helium refrigerators). As such, these accelerators tend to be located in communities and facilities that can support these constraints, such as major accelerator complexes with access to high-voltage electrical equipment, high-volume water cooling systems and/or helium refrigeration, major hospitals or large irradiation facilities for food and mail sterilization. Medical applications of accelerators have been predominantly used for electron acceleration for radiation cancer-treatment therapy. Further proton-beam therapy has been proven very efficacious in treating a variety of cancers with minimal side effects; however, proton-beam therapy is not as widely used as X-ray therapy for treating cancer. This is due to a $100M price tag for each proton accelerator (either a cyclotron or a synchrotron) and the proton beam delivering gantry system. As a result, only a handful of hospitals in the US offer their patients the proton beam therapy option. Unfortunately, the need for advanced care far exceeds the ability to provide it for those communities most in need. Most of the world's population does not reside near a hospital with particle beam therapy based on traditional accelerator designs, thus that population is denied the most advanced medical care available.

Accordingly, there is a need in the art for a compact and robust particle accelerator that can eliminate the structural and operational constraints on the provision of advanced medical care.

SUMMARY

A compact particle accelerator can include two or more cavities disposed along an axis, with each of the cavities being powered by two or more RF drivers. The accelerator can also include multiple cavities each of which is coupled to two or more RF drivers such that a particle beam traveling along the axis is accelerated. The RF drivers can be powered with a commercial power outlet, a low-voltage power supply, battery power, or a combination thereof depending upon the use case. Example configurations of the accelerator include hand held or mobile devices that are capable of delivering a medically-usable beam power (e.g., greater than 1 MeV particle beam energy), thereby distributing advanced medical technologies to a large segment of the human population that has yet to benefit from accelerator technology. Additional features and advantages of the radiation generator of the embodiment are described in detail below with reference to the following drawings.

According to an embodiment of the present invention, there is provided a particle accelerator including: two or more cavities disposed along an axis that are driven independently by solid-state transistor radio frequency (RF) sources; two or more independent RF drivers, each with its own phase and amplitude control, independent of the other RF drivers; and a low-voltage power supply providing power to two or more RF drivers.

Each of the two or more RF drivers may include a high electron mobility transistor (HEMT). Each of the two or more RF drivers may further include a phase shifter coupled to the HEMT. Each of the two or more RF drivers may drive between 300 W and 500 W of RF power to each of the two or more cavities.

Each of the two or more drivers may drive more than 300 W of power to each of the two or more cavities. Each of the two or more drivers may drive between 200 W and 400 W of RF power to each of the two or more cavities. Each of the two or more drivers may drive at least 350 W and 400 W of RF power to each of the two or more cavities.

The power supply may include one or more batteries. The power supply may include commercial power provided through a wall outlet.

The two or more cavities may include more than ten cavities. The two or more cavities may include more than fifteen cavities. The two or more cavities may include more than twenty cavities. The two or more cavities may include more than twenty-five cavities.

Each of the two or more cavities may include a resonant cavity that resonates between 1 GHz and 6 GHz. Each of the two or more cavities may include a resonant cavity that resonates at 5.1 GHz. Each of the two or more cavities may include an accelerating gap distance defined by a ratio of the velocity of a particle in the particle beam to the speed of light.

The particle accelerator may include fifty five cavities and thirty batteries to generate a 1 MeV electron beam. The particle accelerator may be 1.25 m in length along the axis and weigh 30 kg.

The particle accelerator may include one hundred thirty eight cavities and seventy-five batteries to generate a 5 MeV electron beam. The particle accelerator may be 3.1 m in length along the axis of the particle accelerator and weigh 108 kg.

BRIEF DESCRIPTION OF THE DRAWINGS

These and other features and aspects of the present invention will be appreciated and understood with reference to the specification, claims, and appended drawings.

DETAILED DESCRIPTION

As described herein, a compact particle accelerator can provide substantially all of the benefits of a more traditionally configured accelerator, but with substantially reduced size, cost, and weight. In various alternative embodiments described herein, the compact particle accelerator can be configured to be portable and/or handheld, thus permitting the provision of certain advanced medical technologies in remote communities of need. The following description of the embodiments of the invention is not intended to limit the invention to these embodiments, but rather to enable any person skilled in the art to make and use this invention.

Figure 1:
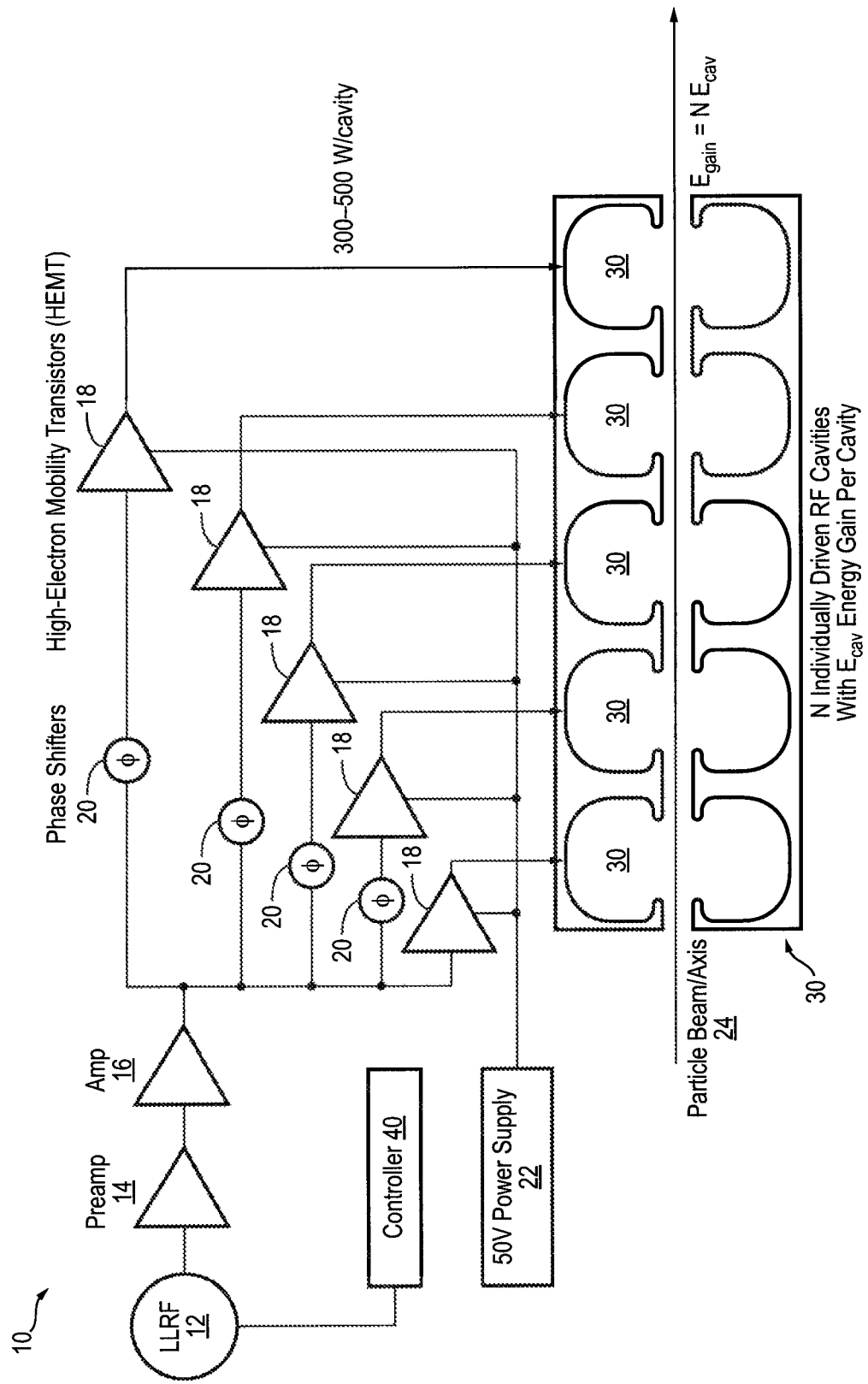
FIG. 1 is a schematic block diagram of a compact particle accelerator in accordance with an embodiment of the present invention.

As shown in FIG. 1, a compact particle accelerator 10 in accordance with an embodiment can include one or more cavities 30 disposed along an axis of the particle accelerator (or along a particle beam of the particle accelerator) 24, each of the cavities 30 is coupled to one or more RF drivers 18. The accelerator 10 can also include a power supply 22 coupled to the one or more RF drivers 18 such that a particle beam 24 traveling along the axis 24 is accelerated. In operation, the accelerator 10 functions to increase the energy of an injected particle beam to a medically-usable level, and to do so in a compact and portable form factor that removes prior use and design constraints of the technology. Depending upon the desired output and configuration, as well as certain trade-offs and improvements in battery technologies, the accelerator 10 can be configured as a hand held or mobile device that is capable of delivering a medically-usable beam power (e.g., 1 MeV electron beam), thereby distributing advanced medical technologies to a large segment of the human population that has yet to benefit from medical accelerator technology.

As shown in FIG. 1, the accelerator 10 can include one or more RF drivers 18 that are coupled each to one or more cavities 30. The RF drivers 18 function to drive RF power into each of the one or more cavities 30 such that a particle beam 24 passing through each of the one or more cavities will receive an increase in total energy, as manifested in a net acceleration of the particles within the particle beam 24. In one variation of the accelerator 10, the one or more RF drivers can include a high electron mobility transistor (HEMT). A HEMT 18 can include any suitable custom or commercially available device that is configured to deliver the requisite voltage/wattage per cavity 30 in the accelerator 10. Example HEMTs 18 can include, for example, a gallium nitride (GaN) HEMT, a wide-bandgap AlGaN/GaN HEMT, and a metamorphic HEMT (AlInAs, GaInAs), or any suitable combination thereof. In one alternative embodiment, the HEMT 18 includes a GaN device that is configured and/or designed to deliver power comparable to 370 W, corresponding to at least 20 keV energy acceleration per cavity 30 in the accelerator 10.

As shown in FIG. 1, in alternative embodiments the accelerator 10 can include a phase shifter 20 coupled to one or more of the drivers 18. The phase shifters 20 function to sequence, align, shift, modify, modulate, and/or control the phase of RF power delivered to each of the RF drivers 18 prior to driving each of the cavities 30. The accelerator 10 can also include a low-level radio frequency (LLRF) controller 12, a preamp 14, and an amplifier 16 coupled to each other and coupled in parallel to each of the one or more phase shifters 20. Alternatively, each of the phase shifters 20 can have its own LLRF controller 12 and preamp 14 directly coupled in series, each being controlled by a separate controller that functions similarly to a circulator 16 or identically to a circulator 16.

As shown in FIG. 1, the accelerator 10 can also include a controller 40 that is configured to control one or more aspects of the operation of the accelerator 10, including for example the phasing of the input power into the one or more drivers 18. In particular, the controller 40 can be configured to control the phasing of the input power by controlling at least the one or more phase shifters 20, as well as the LLRF 12, preamp 14, and/or the amplifier 16. The controller 40 is configured to adapt to operating conditions of the accelerator 10 such that performance is improved or optimized during operation. Suitable feedback measures of operation can include for example field gradients within the one or more cavities 30, the failure of any of the one or more cavities 30, spacing or other geometrical aspects of the one or more cavities 30, presence or changes in an external electromagnetic field, electromagnetic interference, charged/heavy particle interference, or any other suitable measure that can impact the performance of the one or more cavities 30. The controller 40 can detect the phase and amplitude signals from one or more sensors and use a smart algorithm to provide the optimized integral, proportional and differential signals to the LLRF 12. Those of skill in the art will readily appreciate that one or more of these components can be substituted for one or more functionally equivalent electronic and/or controller components without departing from the spirit of the present specification.

As shown in FIG. 1, the accelerator 10 can also include and/or be coupled to a power supply 22. The power supply 22 functions to provide electrical power to the one or more RF drivers 18 such that the latter can drive an acceleration of the particle beam 24. In one variation of the accelerator 10, the power supply 22 can be an integral component of the accelerator 10, such as a portable power supply 22 configured for example as a battery. In another variation of the accelerator 10 of the embodiment, the power supply 22 can be a standard electrical outlet that one would find in a residential or commercial setting that provides the requisite voltage to power the one or more drivers 18. In such a variation of the accelerator 10, the power supply 22 is not integral with the accelerator 10, but rather the accelerator 10 can include components to couple with the power supply (e.g., power cord, wall interface) as well as components to receive, convert, shield, and/or transmit the received power (e.g., AC/DC converter, EMF shielding, circuit breaker) to the one or more drivers 18.

In still other variations of the accelerator 10, the power supply 22 can include both an integrated delivery system (battery) as well as a commercial power conversion system as described herein. For example, a variation of the power supply 22 can include a bank or block of rechargeable batteries as well as an interface for drawing down commercial power for the purpose of either recharging the rechargeable batteries and/or powering the accelerator 10.

According to some embodiments, the power supply 22 can provide a commercially available voltage to the one or more drivers 18. Alternatively, the power supply 22 can provide approximately between 40V and 60V (e.g., between 40V and 60V) to the one or more drivers 18. In still other variations, the power supply 22 can provide approximately 50V (e.g., 50V) to the one or more drivers 18, either as an integrated battery pack, a commercial power converter, or a combination thereof in the form of one or more rechargeable batteries. As those of skill in the art will appreciate, the exact voltage to be supplied by a suitable power supply 22 can depend entirely upon the desired power output of the one or more drivers 18, the power amplification efficiency of the one or more drivers 18, as well as the size and weight design specifications of the desired accelerator. It should be understood that the foregoing description is illustrative of one set of design parameters, and that material and functional improvements in ancillary technologies relating to batteries and drivers can readily result in even lower power, higher efficiency compact acceleration.

As shown in FIG. 1, each of the one or more drivers 18 of the accelerator 10 drives power to each of the one or more cavities 30 to increase the resultant energy in the particle beam 24. In one variation of the accelerator 10, each of the one or more drivers 18 can drive between approximately 300 W and 500 W (e.g., between 300 W and 500 W) of power to each of the one or more cavities 30. In another variation of the accelerator 10, each of the one or more drivers 18 can drive more than 300 W of power to each of the one or more cavities 30. In yet another variation of the accelerator 10, each of the one or more drivers 18 can drive between approximately 200 W and 400 W (e.g., between 200 W and 400 W) of power to each of the one or more cavities 30. In still another variation of the accelerator 10, each of the one or more drivers 18 can drive between approximately 350 W and 400 W (e.g., between 350 W and 400 W) of power to each of the one or more cavities 30. In still another variation of the accelerator 10, each of the one or more drivers 18 can have a variable, non-identical, or customizable drive output based upon the configuration, output, physical design, or geometry of the accelerator 10. Those of skill in the art will readily appreciate that one or more types of driver 18 can be used, for example different types of HEMTs, and therefore one can readily design an accelerator that includes one or more drivers 18 each having a different, variable, or otherwise optimized output power based upon the design specifications of the accelerator 10.

Figure 2:
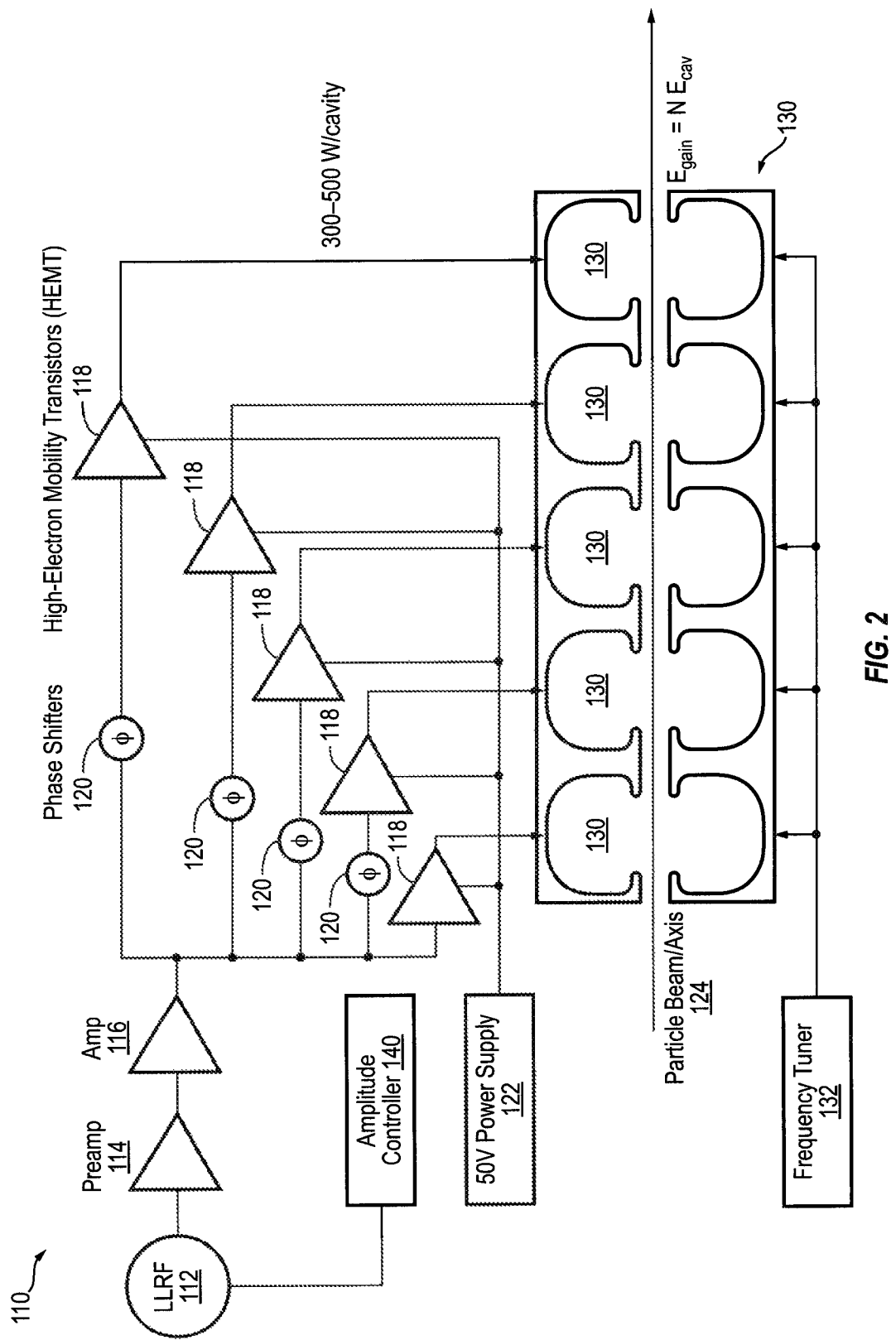
FIG. 2 is a schematic block diagram of a compact particle accelerator in accordance with an alternative embodiment of the present invention.

As shown in FIG. 2, a compact particle accelerator 110 in accordance with an embodiment can include one or more cavities 130 disposed along an axis 124, each of which is coupled to one or more drivers 118. The accelerator 110 can also include a frequency tuner 132 coupled to the picomotors attached to one or more cavities 130. The function of the frequency tuner and picomotors is to adjust the resonance frequency of one or more cavities 130 such that a particle beam 124 traveling along the axis 124 is accelerated continuously. In operation, the accelerator 110 functions to increase the energy of an injected particle beam to a medically-usable level, and to do so in a compact and portable form factor that removes prior use and design constraints of the technology. Depending upon the desired output and configuration, as well as certain trade-offs and improvements in battery technologies, the accelerator 110 can be configured as a hand held or mobile device that is capable of delivering a medically-usable beam power (e.g., 1 MeV electron beam), thereby distributing advanced medical technologies to a large segment of the human population that has yet to benefit from medical accelerator technology.

As shown in FIG. 2, the accelerator 110 can include one or more drivers 118 that are coupled each to one or more cavities 130. The drivers 118 function to drive power into each of the one or more cavities 130 such that a particle beam 124 passing through each of the one or more cavities will receive an increase in total energy, as manifested in a net acceleration of the particles within the particle beam 124. In one variation of the accelerator 110, the one or more drivers can include a high electron mobility transistor (HEMT). A HEMT 118 can include any suitable custom or commercially available device that is configured to deliver the requisite voltage/wattage per cavity 130 in the accelerator 110. Example HEMTs 118 can include, for example, a gallium nitride (GaN) HEMT, a wide-bandgap AlGaN/GaN HEMT, and a metamorphic HEMT (AlInAs, GaInAs), or any suitable combination thereof. In one alternative embodiment, the HEMT 118 includes a GaN device that is configured and/or designed to deliver power comparable to 370 W, corresponding to at least 20 keV energy acceleration per cavity 130 in the accelerator 110.

As shown in FIG. 2, in alternative embodiments the accelerator 110 can include a phase shifter 120 coupled to one or more of the drivers 118. The phase shifters 120 function to sequence, align, shift, modify, modulate, and/or control the delivery of power to each of the drivers 118 prior to driving each of the cavities 130. The accelerator 110 can also include a microwave oscillator 112 coupled to each of the one or more phase shifters 120. Alternatively, each of the phase shifters 120 can have its own microwave oscillator 112 directly coupled thereto.

As shown in FIG. 2, the accelerator 10 can also include a controller 140 that is configured to control one or more aspects of the operation of the accelerator 110, including for example the phasing of the input power into the one or more drivers 118. In particular, the controller 140 can be configured to control the phasing of the input power by controlling at least the one or more phase shifters 120, as well as the microwave oscillator 112. The controller 140 is configured to adapt to operating conditions of the accelerator 110 such that performance is optimized during operation. Suitable feedback measures of operation can include for example field gradients within the one or more cavities 130, the failure of any of the one or more cavities 130, spacing or other geometrical aspects of the one or more cavities 130, presence or changes in an external electromagnetic field, electromagnetic interference, charged/heavy particle interference, or any other suitable measure that can impact the performance of the one or more cavities 130. The controller 140 can detect the phase and amplitude signals from one or more sensors and use a smart algorithm to provide the improved or optimized integral, proportional and differential signals to the microwave oscillator 112. The controller 140 can also provide signal to the frequency tuner 132 to adjust the resonance frequency of one or more cavities 130 to achieve continuous energy gain from one cavity to the next. Those of skill in the art will readily appreciate that one or more of these components can be substituted for one or more functionally equivalent electronic and/or controller components without departing from the spirit of the present specification.

As shown in FIG. 1, the accelerator 110 can also include and/or be coupled to a power supply 122. The power supply 122 functions to provide electrical power to the one or more drivers 118 such that the latter can drive an acceleration of the particle beam 124. In one variation of the accelerator 110, the power supply 122 can be an integral component of the accelerator 110, such as a portable power supply 122 configured for example as a battery. In another variation of the accelerator 110 of the embodiment, the power supply 122 can be a standard electrical outlet that one would find in a residential or commercial setting that provides the requisite voltage to power the one or more drivers 118. In such a variation of the accelerator 110, the power supply 122 is not integral with the accelerator 110, but rather the accelerator 110 can include components to couple with the power supply (e.g., power cord, wall interface) as well as components to receive, convert, shield, and/or transmit the received power (e.g., AC/DC converter, EMF shielding, circuit breaker) to the one or more drivers 118.

In still other variations of the accelerator 110, the power supply 122 can include both an integrated delivery system (battery) as well as a commercial power conversion system as described herein. For example, a variation of the power supply 122 can include a bank or block of rechargeable batteries as well as an interface for drawing down commercial power for the purpose of either recharging the rechargeable batteries and/or powering the accelerator 110.

According to some embodiments, the power supply 122 can provide a commercially available voltage to the one or more drivers 118. Alternatively, the power supply 122 can provide approximately between 40V and 60V (e.g., between 40V and 60V) to the one or more drivers 118. In still other variations, the power supply 122 can provide approximately 50V (e.g., 50V) to the one or more drivers 118, either as an integrated battery pack, a commercial power converter, or a combination thereof in the form of one or more rechargeable batteries. As those of skill in the art will appreciate, the exact voltage to be supplied by a suitable power supply 122 can depend entirely upon the desired power output of the one or more drivers 118, the power amplification efficiency of the one or more drivers 118, as well as the size and weight design specifications of the desired accelerator. It should be understood that the foregoing description is illustrative of one set of design parameters, and that material and functional improvements in ancillary technologies relating to batteries and drivers can readily result in even lower power, higher efficiency compact acceleration.

As shown in FIG. 1, each of the one or more drivers 118 of the accelerator 110 drives power to each of the one or more cavities 130 to increase the resultant energy in the particle beam 124. In one variation of the accelerator 110, each of the one or more drivers 118 can drive between approximately 300 W and 500 W (e.g., between 300 W and 500 W) of power to each of the one or more cavities 30. In another variation of the accelerator 110, each of the one or more drivers 118 can drive more than 300 W of power to each of the one or more cavities 130. In yet another variation of the accelerator 110, each of the one or more drivers 118 can drive between approximately 200 W and 400 W (e.g., between 200 W and 400 W) of power to each of the one or more cavities 130. In still another variation of the accelerator 110, each of the one or more drivers 118 can drive between approximately 350 W and 400 W (e.g., between 350 W and 400 W) of power to each of the one or more cavities 130. In still another variation of the accelerator 110, each of the one or more drivers 118 can have a variable, non-identical, or customizable drive output based upon the configuration, output, physical design, or geometry of the accelerator 110. Those of skill in the art will readily appreciate that one or more types of driver 118 can be used, for example different types of HEMTs, and therefore one can readily design an accelerator that includes one or more drivers 118 each having a different, variable, or otherwise optimized output power based upon the design specifications of the accelerator 110.

Figure 3:
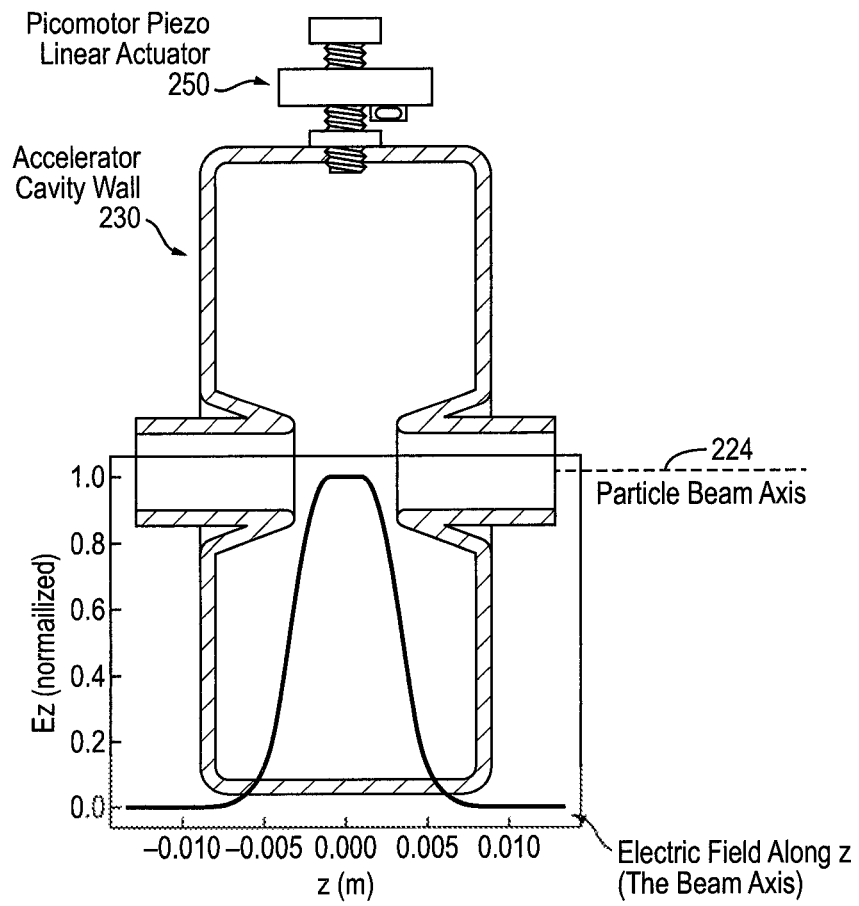
FIG. 3 is a cross-sectional diagram of a cavity of a compact particle accelerator in accordance with an alternative embodiment of the present invention.

As shown in FIG. 3, the accelerator 10 can include one or more cavities 30 each connected to one of the one or more drivers 18. Each of the cavities 30 is oriented about an axis 24 that is coincident or collinear with a particle beam 24 as shown in FIG. 1. The cavities 30 function to contain, direct, amplify, increase, resonate, and/or accelerate the momentum/energy of a particle beam 24 by assisting or controlling the conversion of inbound power from the one or more drivers 18 (e.g., RF power) to kinetic energy imparted into the particles within the particle beam 24. As described herein, the accelerator 10 can include one or more cavities 30 aligned along the particle beam 24 such that each cavity 30, being individually driven, can impart a substantial amount of energy into the particle beam 24 thereby yielding a significant increase the output power of the particle beam 24. As each cavity 30 can be relatively compact and lightweight, a fully functional and accelerator 10 can be designed and built with a relatively modest footprint in terms of size, weight, and power. In one variation of the accelerator 10 of the embodiment, the one or more cavities 30 can include more than ten cavities 30. In another variation of the accelerator 10 of the embodiment, the one or more cavities 30 can include more than fifteen cavities 30. In still another variation of the accelerator 10 of the embodiment, the one or more cavities 30 can include more than twenty cavities 30. In another variation of the accelerator 10 of the embodiment, the one or more cavities 30 can include more than twenty-five cavities 30. In still other variations of the accelerator 10 of the embodiment, the one or more cavities 30 can include more than 30, more than 50, or more than 100 cavities. Particular example embodiments described herein illustrate two configurations with dozens of cavities 30 that still provide for very compact and mobile operation of the accelerator 10.

Cavities according to embodiments of the present invention may be any suitable type of accelerator cavity.

As shown in FIG. 3, a cavity 30 can include a resonant cavity that defines a geometry within which an electric field can resonate, such as for example an inbound electric field driven by the one or more drivers 18. As shown in FIG. 3, a graphical overlay of electric field as a function of distance illustrates a single wave resonant within the cavity 230, with a peak approximately in the middle of the cavity 230 (e.g., in the middle of the cavity 230). The one or more cavities 230 include a resonant cavity that resonates at approximately between 4 GHz and 6 GHz (e.g., between 4 GHz and 6 GHz). Alternatively, each of the one or more cavities 230 can include a picomotor piezo linear actuator 250 that moves under the control of the frequency tuner 132. The function of the picomotor piezo linear actuator 250 that is attached to outer part of the accelerator cavity wall 230 is to provide remote and real-time adjustment of the resonance frequency of the accelerator cavity 230. In another variation of the accelerator 10, each of the one or more cavities 230 can include and/or define an accelerating gap distance defined by a ratio of the velocity of a particle in the particle beam 224 to the periodicity of the particle beam 224.

Example Configurations

Figure 4:
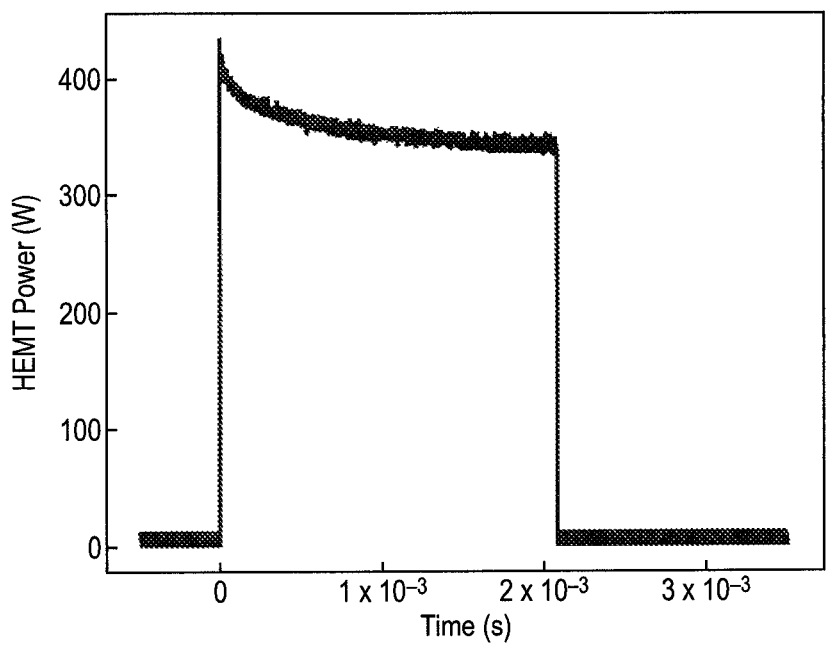
FIG. 4 is a graphical representation of a power curve of a component of a compact particle accelerator in accordance with an alternative embodiment of the present invention.
Figure 5:
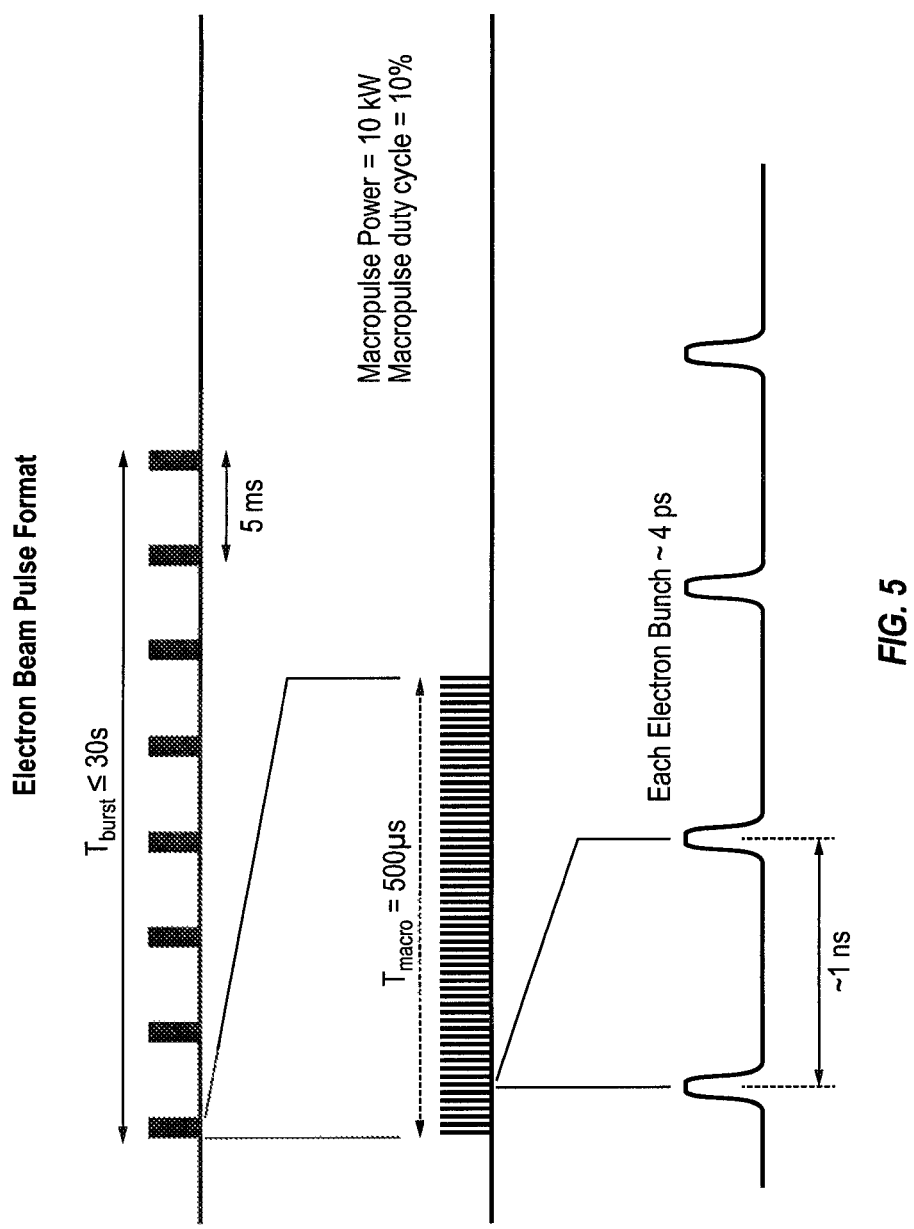
FIG. 5 is a graphical representation of a beam pulse shape of a compact particle accelerator in accordance with an alternative embodiment of the present invention.

As also shown in FIG. 1, example configurations of the accelerator 10 of the embodiment, the one or more drivers 18 can include HEMT drivers, each providing a drive of approximately 370 W per cavity. A power output per HEMT device as a function of time is shown in FIG. 4, wherein the average 370 W occurs at approximately $1 \times 10^{-3}$ seconds. Given the foregoing, each of the one or more cavities 30 can be expected to add approximately 20 keV of energy to the particle beam 24. As such, approximately fifty cavities 30 aligned in series will yield a 1 MeV particle beam 24. An example electron beam pulse format is shown in FIG. 5 for a representative output particle beam with a peak power of approximately 10 kW at 10% duty cycle. Accordingly, given a relatively low input power of an example electron beam (10 kW) and a modest control voltage (50V power supply 20), given enough serially disposed cavities 30 and high gain drivers 18, it is possible to generate a 1 MeV or greater particle beam 24 from a lightweight accelerator with a relatively small physical footprint.

Figure 6A:
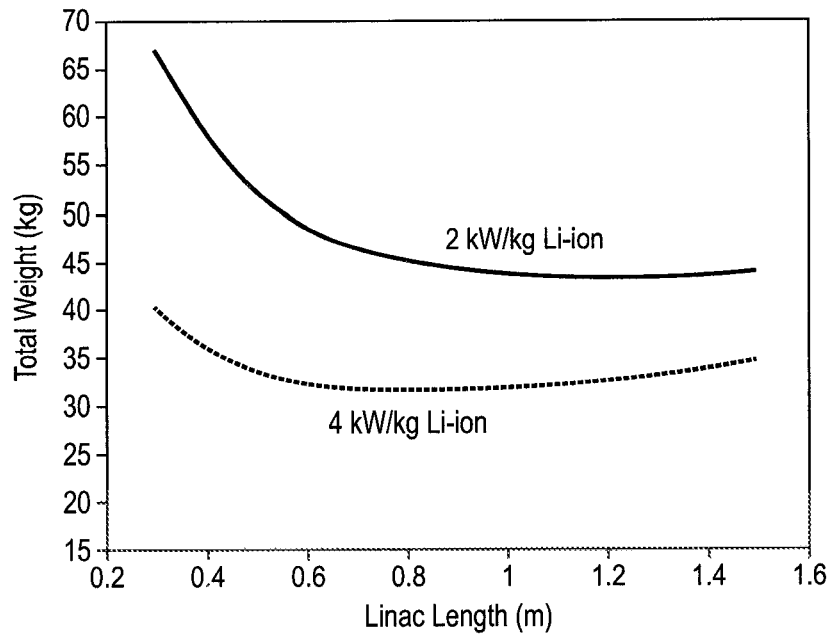
FIG. 6A is a graphical representation of a size/weight/power curve of a compact particle accelerator in accordance with an alternative embodiment of the present invention.
Figure 6B:
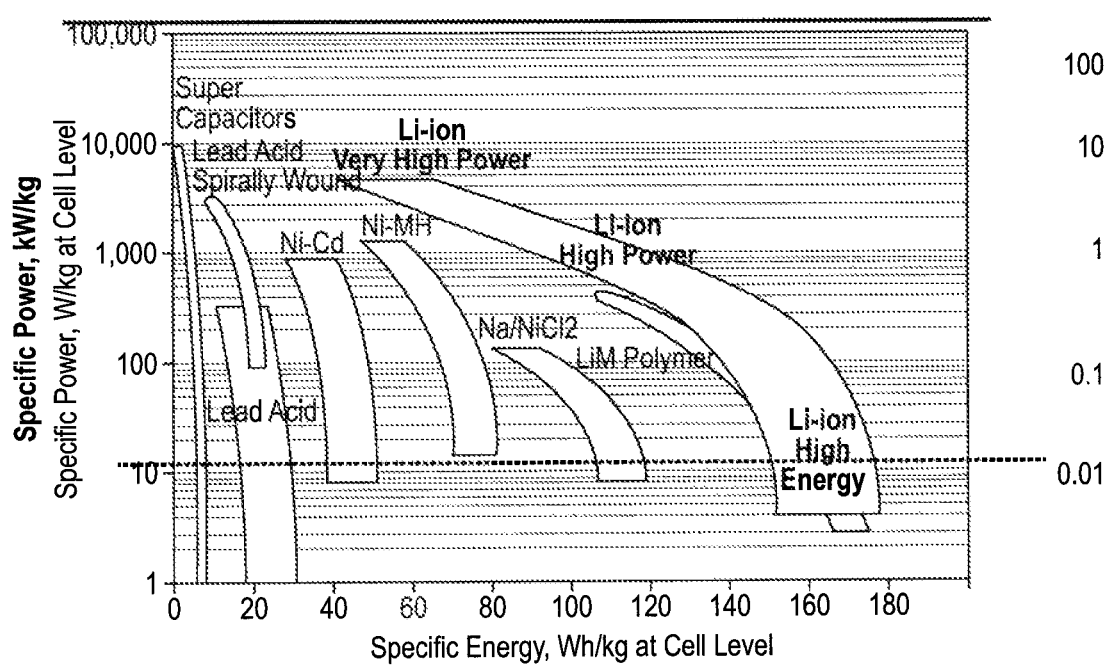
FIG. 6B is a graphical representation of a power/energy curve for various power sources of a compact particle accelerator in accordance with an alternative embodiment of the present invention.

In another example embodiment of the accelerator 10, the power supply 20 includes batteries or battery banks arranged in series to increase the DC voltage to the level needed to drive the RF drivers (for instance, a bank of eight lithium batteries in series will provide 50 volts DC) that permit the accelerator 10 to be portable and usable in remote or rural locations. FIGS. 6A and 6B are illustrative of the inherent tradeoffs in size, weight, and power that are current design constraints given the state of the art in both battery technology and driver 18 gain. As shown in FIG. 6A, at or around 1 meter in overall length of the accelerator 10, the weight per length tends to flatten out, with 2 kW/kg Li-ion batteries adding relatively more weight to the overall device. However, those of skill in the art will readily note that even at 1.5 meters in length, the heavier of the two battery configurations still weighs in at a relatively slight 45 kg, which is more than light enough to be assembled and deployed as a portable accelerator 10 in any number of applications. FIG. 6B illustrates various power/energy/weight curves for different types of power sources on a logarithmic scale. The Li-ion power sources of various kinds (very high power, high power, high energy) display the greatest range. Those of skill in the art will appreciate that advances in either battery technology or driver technology, separately or together, can still further improve the performance of accelerator 10 while keeping within the scope of the fundamental design parameters described herein.

Figure 7A:
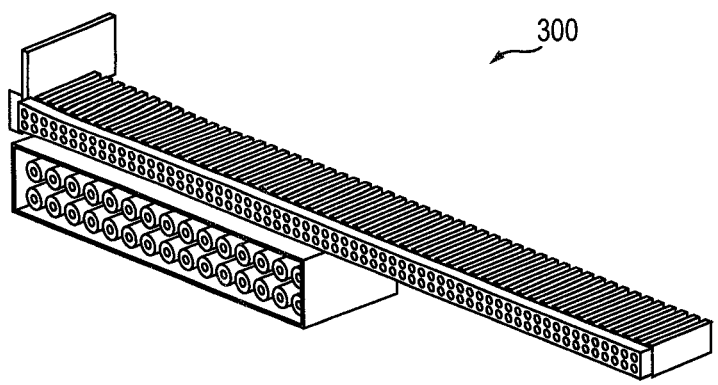
FIG. 7A is a perspective view of an example embodiment of a compact particle accelerator in accordance with an alternative embodiment of the present invention.
Figure 7B:
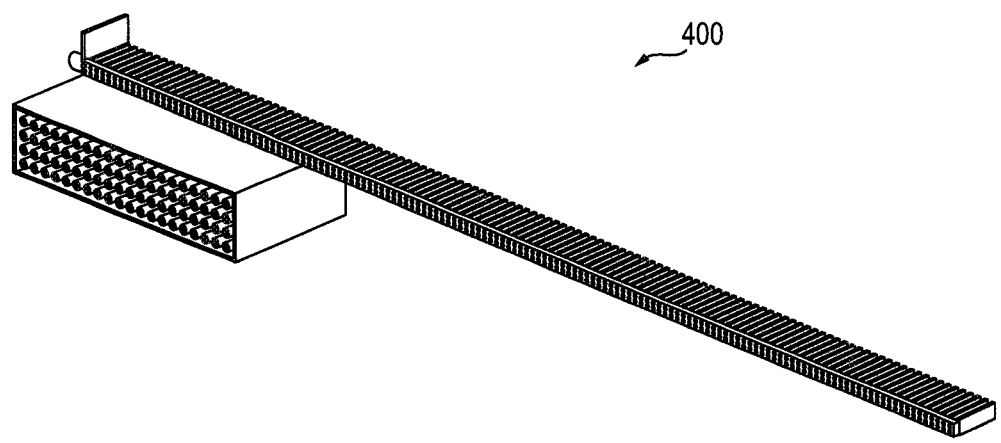
FIG. 7B is a perspective view of an example embodiment of a compact particle accelerator in accordance with another alternative embodiment of the present invention.

FIGS. 7A and 7B are perspective views of alternative example embodiments of the accelerator 10 of the embodiment. FIG. 7A illustrates an example accelerator 300 that includes fifty five cavities and thirty lithium batteries arranged in series to provide 50V DC to power the RF drivers to generate approximately a 1 MeV electron beam. The example accelerator 300 is approximately 1.25 m in length along the axis and weighs approximately 30 kg. FIG. 7B illustrates a second example accelerator 400 that includes one hundred thirty eight cavities and eighty batteries to generate approximately a 5 MeV electron beam. The second example accelerator 400 is approximately 3.1 m in length along the axis and weighs approximately 108 kg. As illustrated in the example configurations, substantial power and portability can be readily devised using the principles set forth in describing the accelerator 10 of the embodiment and variations thereof. Such improvements in power and portability have the potential to greatly increase the availability and efficacy of medical technologies throughout all aspects of the population, including especially those in remote and rural areas who have been deprived of its benefit until the present invention.

The configurations shown in FIGS. 7A and 7B are for electron beams with two maximum energies (1 and 5 MeV). However, the configurations are sufficiently flexible to operate at energies below the maximum by turning off the HEMT drivers for certain accelerating cavities in order to tune the electron beam energy to meet a specific application.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present invention.

It will be understood that when an element or layer is referred to as being "on," "connected to," or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments and is not intended to be limiting of the present invention. As used herein, the singular forms "a" and "an" are intended to include the plural forms as well, unless the context clearly indicates otherwise. It will be further understood that the terms "comprises," "comprising," "includes," and "including," when used in this specification, specify the presence of the stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list.

As used herein, the term "substantially," "about," and similar terms are used as terms of approximation and not as terms of degree, and are intended to account for the inherent variations in measured or calculated values that would be recognized by those of ordinary skill in the art. Further, the use of "may" when describing embodiments of the present invention refers to "one or more embodiments of the present invention." As used herein, the terms "use," "using," and "used" may be considered synonymous with the terms "utilize," "utilizing," and "utilized," respectively. Also, the term "exemplary" is intended to refer to an example or illustration.

The electronic or electric devices (e.g., controllers) and/or any other relevant devices or components according to embodiments of the present invention described herein may be implemented utilizing any suitable hardware, firmware (e.g. an application-specific integrated circuit), software, or a combination of software, firmware, and hardware. For example, the various components of these devices may be formed on one integrated circuit (IC) chip or on separate IC chips. Further, the various components of these devices may be implemented on a flexible printed circuit film, a tape carrier package (TCP), a printed circuit board (PCB), or formed on one substrate. Further, the various components of these devices may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the spirit and scope of the exemplary embodiments of the present invention.

While this invention has been described in detail with particular references to and illustrative embodiments thereof, the embodiments described herein are not intended to be exhaustive or to limit the scope of the invention to the exact forms disclosed. Persons skilled in the art and technology to which this invention pertains will appreciate that alterations and changes in the described structures and methods of assembly and operation can be practiced without meaningfully departing from the principles, spirit, and scope of this invention, as set forth in the following claims and equivalents thereof.

What is claimed is:

1. A particle accelerator comprising:
   a plurality of cavities along an axis of the particle accelerator, each of the plurality of cavities comprising a linear actuator;
   a plurality of radio frequency (RF) drivers, each of the plurality of RF drivers configured to be phase and amplitude control independent of other ones of the RF drivers, wherein the plurality of RF drivers are to drive the plurality of cavities, each of the plurality of cavities being configured to be independently driven of other ones of the cavities; and
   a frequency tuner coupled to the linear actuator of each of the plurality of cavities, the frequency tuner being to adjust resonance frequency of a cavity of the plurality of cavities by controlling the linear actuator of the cavity in real time.

2. The particle accelerator of claim 1, wherein the linear actuator is to provide remote and real time adjustment of the resonant frequency of the cavity.

3. The particle accelerator of claim 1, wherein the particle accelerator further comprises a low-voltage power supply to power the plurality of RF drivers, wherein the low-voltage power supply comprises one or more batteries or commercial power sources through wall outlets.

4. The particle accelerator of claim 1, wherein each of the plurality of RF drivers comprises a high electron mobility transistor (HEMT) and a phase shifter coupled to the HEMT, and wherein each of the plurality of cavities has an accelerating gap distance defined by a ratio of a velocity of a particle in a particle beam of the cavity, to speed of light.

5. The particle accelerator of claim 1, wherein each of the plurality of RF drivers is configured to drive between 300 W and 500 W of RF power to each of the plurality of cavities.

6. The particle accelerator of claim 1, wherein each of the plurality of RF drivers is configured to drive more than 300 W of power to each of the plurality of cavities.

7. The particle accelerator of claim 1, wherein each of the plurality of RF drivers is configured to drive between 200 W and 400 W of RF power to each of the plurality of cavities.

8. The particle accelerator of claim 1, wherein each of the plurality of RF drivers is configured to drive at least 350 W and 400 W of RF power to each of the plurality of cavities.

9. The particle accelerator of claim 1, wherein the plurality of cavities comprise more than ten cavities.

10. The particle accelerator of claim 1, wherein the plurality of cavities comprise more than fifteen cavities.

11. The particle accelerator of claim 1, wherein the plurality of cavities comprise more than twenty cavities.

12. The particle accelerator of claim 1, wherein the plurality of cavities comprise more than twenty-five cavities.

13. The particle accelerator of claim 1, wherein each of the plurality of cavities comprises a resonant cavity configured to resonate between 1 GHz and 6 GHz.

14. The particle accelerator of claim 1, wherein each of the plurality of cavities comprises a resonant cavity configured to resonate at 5.1 GHz.

15. A particle accelerator comprising:
    a plurality of cavities along an axis of the particle accelerator;
    a plurality of radio frequency (RF) drivers, each of the plurality of RF drivers configured to be phase and amplitude control independent of other ones of the RF drivers, wherein the plurality of RF drivers are to drive the plurality of cavities, each of the plurality of cavities being configured to be independently driven of other ones of the cavities;
    a low-voltage power supply to power the plurality of RF drivers; and
    a frequency tuner coupled to a linear actuator of each of the plurality of cavities, the frequency tuner being to adjust resonance frequency of a cavity of the plurality of cavities by controlling the linear actuator of the cavity, wherein the linear actuator is to provide remote and real time adjustment of the resonant frequency of the cavity.

16. The particle accelerator of claim 15, wherein the plurality of cavities comprise at least fifty five cavities and the low-voltage power supply comprises at least thirty batteries.

17. The particle accelerator of claim 16, wherein the fifty five cavities and the thirty batteries are to generate a 1 MeV electron beam along the axis of the particle accelerator, and wherein the particle accelerator is at least 1.25 m in length along the axis of the particle accelerator and weighs at least 30 kg.

18. The particle accelerator of claim 15, wherein the plurality of cavities comprise at least one hundred thirty eight cavities and the low-voltage power supply comprises at least seventy-five batteries, and the one hundred thirty eight cavities and the seventy-five batteries are to generate a 5 MeV electron beam.

19. The particle accelerator of claim 18, wherein the particle accelerator is not more than 3.1 m in length along the axis of the particle accelerator and weighs not more than 108 kg.

20. A method of operating a particle accelerator, the method comprising:
   controlling, a plurality of radio frequency (RF) drivers, each of the plurality of RF drivers being phase and amplitude control independent of other ones of the RF drivers;
   driving, a plurality of cavities along an axis of the particle accelerator via the plurality of RF drivers, each of the plurality of cavities comprising a linear actuator and being independently driven of other ones of the cavities;
   powering, the plurality of RF drivers via a low-voltage power supply; and
   adjusting, resonance frequency of a cavity of the plurality of cavities by controlling a frequency tuner coupled to the linear actuator of each of the plurality of cavities, the frequency tuner being to control the linear actuator of the cavity to provide remote and real time adjustment of the resonant frequency of the cavity.

* * * * *